US005725869A

United States Patent [19]

Lo

[11] Patent Number: 5,725,869
[45] Date of Patent: Mar. 10, 1998

[54] MICROSPHERE RESERVOIRS FOR CONTROLLED RELEASE APPLICATION

[75] Inventor: Ray J. R. Lo, San Leandro, Calif.

[73] Assignee: Zeneca Limited, London, England

[21] Appl. No.: 736,266

[22] Filed: Oct. 24, 1996

Related U.S. Application Data

[63] Continuation of Ser. No. 262,416, Jun. 20, 1994, abandoned.

[51] Int. Cl.$^6$ .................................................. A61K 9/52
[52] U.S. Cl. ......................... 424/408; 424/401; 424/450
[58] Field of Search ........................... 424/408, 401, 424/450

[56] References Cited

U.S. PATENT DOCUMENTS

| 4,780,320 | 10/1988 | Baker | 424/493 |
| 5,064,949 | 11/1991 | Steiner | 536/56 |
| 5,288,502 | 2/1994 | McGinty et al. | 424/489 |

OTHER PUBLICATIONS

Ghebre–Sallassie et al., Pharmaceutical Technology p. 97, Sep. 1988.
Itoh et al., Chem. Pharm. Bull. 28, 2816 (1980).
Sakellariou et al., J. Controlled Release 7, 147 (1988).
Safwat et al., J. Controlled Release 9, 65 (1989).
Benita et al., J. Controlled Release 12, 213 (1990).
Watts et al., J. Controlled Release 16, 311 (1991).
Moldenhauer et al., J. Controlled Release 17, 49 (1991).
Tefft et al., Proc. Intern. Symp. Control. Rel. Bioact. Mater. 19, 1992.
Lohmann, Proc. Intern. Symp. Control. Rel. Bioact. Mater. 19, 170 (1992).

*Primary Examiner*—Thurman K. Page
*Assistant Examiner*—D. Faulkner
*Attorney, Agent, or Firm*—Cushman Darby & Cushman IP Group Pillsbury Madison & Sutro LLP

[57] ABSTRACT

Microspheres, optionally containing an ingredient to be dispensed through controlled release, are prepared by solvent evaporation of an oil-in-water emulsion formed from an organic solvent containing a polymer and a plasticizer and an aqueous solution containing one or more emulsifying agents. The microcapsules formed have a size of between about 3 and about 300 microns in diameter and are porous and spongy in structure as opposed to the hollow core, relatively solid surface structure of microspheres formed by solvent evaporation without utilizing a plasticizer. The microspheres can have a relatively high loading rate of an ingredient to be dispensed combined with a relatively low release rate and are useful for instance for agricultural chemicals, pharmaceuticals or medicines, cosmetics or fragrances.

19 Claims, No Drawings

MICROSPHERE RESERVOIRS FOR CONTROLLED RELEASE APPLICATION

This is a continuation of application Ser. No. 08/264,416, filed on Jun. 20, 1994 now abandoned, which was abandoned upon the filing hereof.

BACKGROUND AND PRIOR ART

This invention relates to controlled-release compositions in the form of microspheres containing one or more ingredients to be dispensed at a controlled rate, and to the microspheres themselves. Controlled-release formulations are used in a number of industries and for a number of types of products such as agricultural products (fertilizers, pesticides, soil nutrients, etc.), drugs and pharmaceuticals, fragrances and cosmetics. Controlled-release formulations permit the application of a product containing a relatively concentrated amount of an ingredient which is to be dispensed (sometimes referred to as the "active ingredient"), which is then applied or dispensed relatively slowly and over a relatively long period of time. This permits, for instance, the application of a pesticide or a pharmaceutical over a long period of time to effect a steady treatment as opposed to a quick release of the ingredient, which may result in initially supplying more material than is needed, or having an insufficient amount of material available at a later time. The use of controlled-release formulations also permits the application and handling of materials containing a higher concentration of active ingredient while minimizing the possible toxicity consequences of such concentration, since the exposure to the active ingredient is relatively limited in amount at a given time.

There are a number of different types of controlled-release formulations. One such type involves encasing or encapsulating the active ingredient in microspheres. In agriculture, microspheres containing active ingredients may be produced which are dispersible in water so as to be used in conventional spraying equipment.

One technique for producing microspheres is known as the "solvent evaporation" technique or process. In that type of process, an active ingredient is dissolved in a solvent, along with additives and is mixed with an aqueous solution containing a polymer which will form an encapsulating spherical wall. The mixture is in the form of an oil-in-water emulsion, with the organic phase in the form of droplets of a polymer surrounding a solution of the active ingredient. The solvent (together with the water) is then evaporated to form microspheres. A typical process of this type is described in the paper by Tefft, et al, Proc. Int. Smyp. Control. Rel. Bioact. Mater., page 19 (1992), entitled "Microspheres for Controlled-Release Herbicide Formulations". That article describes preparation of microspheres composed of ethyl cellulose or polyarylsulfone polymer including the herbicide dicamba as the active ingredient, by dissolving dicamba and the polymer in methylene chloride, emulsifying that solution into an aqueous solution containing polyvinyl alcohol and sodium dodecyl sulfate, stirring and evaporating the solvent under vacuum.

It has been found, however, that production of microspheres by the solvent evaporation method can result in microspheres which, while permitting controlled release, nevertheless permit too rapid a release of the active ingredient. An overly rapid release may be undesirable in a given situation for the reasons mentioned above, for instance it provides an overdose of, or wastes, the active ingredient.

SUMMARY OF THE INVENTION

This invention comprises the production of microspheres of an ingredient to be dispensed by the solvent evaporation method in which a plasticizer selected from the group consisting of phthalate esters, phosphate esters, citrate esters, sebacate esters, glycerol, triacetin, and acetylated monoglyceride, is included.

In another aspect, this invention comprises a process for producing microspheres containing an ingredient to be dispensed comprising: (a) Preparing an organic phase comprising a solution of an ingredient to be dispensed, a polymer and a plasticizer selected from the group consisting of phthalate esters, phosphate esters, citrate esters, sebacate esters, glycerol, triacetin or acetylated monoglyceride, in an organic solvent; (b) preparing an aqueous phase comprising an aqueous solution of an emulsifying agent; (c) combining the organic and aqueous phases under emulsifying conditions to form an emulsion of the organic phase in the aqueous phase; and (d) evaporating the solvent to form microspheres comprising the polymer, the plasticizer and the ingredient to be dispensed.

In yet another aspect, this invention comprises a process for production of microspheres which are "blank", i.e. do not contain an ingredient to be dispensed. Such blank microspheres can be loaded at a subsequent time with one or more active ingredients.

The invention herein comprises both the processes mentioned above as well as the products of said processes, blank microspheres or microspheres containing the ingredient to be dispensed.

DETAILED DESCRIPTION OF THE INVENTION

Production of the microspheres of this invention is carried out using the solvent-evaporation technique, generally described above, but with the additional inclusion of a plasticizer.

In this process, two solutions are prepared: An organic solution containing a polymer, a plasticizer and (when the microspheres are to be produced "loaded") material to be dispensed ("active ingredient"), and an aqueous solution containing an emulsifying agent. This solution may contain polyvinyl alcohol, which may serve as an emulsifying agent and/or to control viscosity. The two solutions are then combined under conditions so as to form an emulsion of the organic phase in the aqueous phase, which is then converted to an encapsulated product comprising microspheres composed of a polymer and plasticizing agent (and containing the ingredient to be dispensed), by evaporating the solvent, either under heat or vacuum.

The polymer utilized in the process according to this invention may be selected from a wide number of types known to be useful in producing controlled-release formulations. These include both synthetic polymers as well as naturally-occurring polymers and their derivatives.

Synthetic polymers include, for instance, vinyl polymers, polyamides, polyureas, polyurethanes, polyesters, acrylates, methacrylates, polyarylsulfone, acrylatemethacrylate copolymers, and poly(ethylene oxide) polymeric resins such as those sold under the trademark POLYOX.

Naturally-occurring polymers and their derivatives include materials such as cellulosic materials, starches, lignins, vegetable gums, alginates, and derivatives thereof such as polysaccharides, proteins, shellac, and resins. The polymer may also be a blend of one or more of the above synthetic or naturally-occurring materials.

The plasticizer utilized in the process of this invention is selected from phthalate esters, phosphate esters, citrate esters, sebacate esters, glycerole, triacetin, and acetylated monoglyceride. Examples of plasticizers of the above types include dimethyl, diethyl, dipropyl, dibutyl, dibutoxyethyl and dioctyl phthalates; tricresyl and triphenyl phosphates; triethyl, tributyl, and acetyl tributyl citrates; and dibutyl sebacate.

Preferred polymers for use in the process according to this invention are cellulosic polymers and derivatives thereof. Preferred plasticizers are phthalate esters.

The choice of plasticizer for use with a given polymer is within the skill of those in the art and, in general, any of the types of plasticizers mentioned above may be combined or used with any of the polymers mentioned above, with the choice of plasticizer being made to achieve optimum effects.

The ingredient to be dispensed may be a chemical or other ingredient for use in agriculture, a pharmaceutical or other medicinal ingredient, a fragrance, a cosmetic, or any other type of ingredient for which a controlled release or dispensing is desirable. Agricultural materials include pesticides (for instance herbicide, insecticides, fungicides, bactericides and the like), plant growth regulators, fertilizers, and soil nutrients. The microspheres may contain more than one ingredient to be dispensed, for instance a combination of two or more pesticides or two or more pharmaceuticals.

Preferred agricultural materials include the pesticides lambda-cyhalothrin [1α(S*),3α(Z)]-(±)cyano-(3-phenoxybenzyl)-(2-chloro-3,3,3-trifluoro-1-propenyl)-2,2-dimethylcyclopropane carboxylate, paraquat [1,1'-dimethyl-4,4'-bipyridinium dichloride or other salts], napropramide (N,N-diethyl-2-(α-naphthoxy)propionamide) and fluazifop-butyl {butyl (R or RS)-2-[4-[[5-(trifluoromethyl)-2-pyridinyl]oxy]phenoxy]propanoate}.

The solvent utilized in the process is chosen from among typical solvents on the basis of three properties. First, the solvent must dissolve the polymer, the plasticizer and the ingredient to be dispensed (if the microspheres are to be produced "loaded"). Secondly, the solvent preferably should have a relatively low boiling point so as to be easily removed through evaporation. Thirdly, the solvent must be water-immiscible. Suitable solvents include hydrocarbons such as pentane, hexane, heptane, cyclohexane and the like, and chlorinated solvents such as dichloromethane.

The emulsifying agent may be any of a number of types known to cause emulsions to form when organic and aqueous phases are mixed. Typical emulsifying agents include surfactants such as polyethylene glycol ethers of linear alcohols, ethoxylated nonylphenols, naphthalene sulfonates, ethylene oxide/propylene oxide block copolymers, alkali metal/alkyl sulfates and other salts, and the like.

The organic phase will typically contain from about 1 to about 50 weight percent polymer and from about 0.1 to about 20 weight percent plasticizer, depending on the nature of the polymer, plasticizer and solvent. The aqueous phase will typically contain from about 0.1 to about 20 weight percent of emulsifying agent and optionally from about 1 to about 30 weight percent polyvinyl alcohol. The composition of the final microsphere product will be from about 5 to about 80 weight percent polymer, from about 0.5 to about 10 weight percent of the plasticizer, and up to about 70 weight percent of the ingredient to be dispensed. The microspheres will be from about 3 to about 300 microns in diameter.

Production of microspheres using cellulosic polymers (for example ethyl cellulose) by the solvent-evaporation method is not new. For instance, production of very small microspheres (0.2–1 microns diameter) from plasticized ethyl cellulose polymers is described by Ghebre-Sellassie et al., Pharmaceutical Technology, page 96 (September 1988). Such microspheres, however, were produced for use in a controlled-release film to be coated over an ingredient to be dispensed rather than to contain the ingredient. Additionally, such microspheres, which are approximately 0.2–1 micron diameter, are much smaller than those of the present invention (between about 3 and about 300 microns diameter).

The Tefft et al. work, on the other hand, does produce microspheres of sizes similar to those produced by the present invention, and which did contain an ingredient to be dispensed (dicamba herbicide). However, it was found that the spheres produced by Tefft et al., who did not use a plasticizer, were in the shape of thin-walled hollow spheres containing dicamba whereas those produced by the present process are not hollow spheres, but have a spongy structure which may permit the ingredient to be released at a slower rate. Advantages of such a slower dispensing rate include lower toxicity of material to handlers, and a more controlled use of ingredient.

Because of their spongy structure, the miocrospheres of this invention (as opposed to the hollow spheres of Tefft et al.) may be produced "blank", that is without containing an ingredient to be dispensed. Such ingredient may be added at a later date, for instance by soaking or dipping the microspheres in a solution of the ingredient, spraying the ingredient on the spheres or mixing the ingredient and spheres in a mixer. Blank microspheres are produced by carrying out the process as described herein except that an ingredient to be dispensed is not included.

The production of blank microspheres to be loaded later will be advantageous in several situations. For example, if long-term storage of encapsulated products is likely to occur, the active ingredient could begin to migrate out of the capsules during storage. Production of blank capsules would permit separate long-term storage of the capsules and the active ingredient, with the vinyl "loaded" product produced relatively shortly before expected use. Also, production of blank microspheres may be advantageous in a multi-product plant in which microspheres are to be loaded with different ingredients to be dispensed.

The size of the microspheres depends to a great extent on the speed with which the emulsion is stirred. The higher the stirring speed, the smaller the droplet of active ingredient plus polymer formed in the aqueous solution. Preferred stirring speeds are 500–2,500 rpm. The resulting microspheres form a dry, free-flowing powder which can have a high loading of the active ingredient or ingredient to be dispensed. Furthermore, the process for the production can be carried out at room temperature and does not require elevated temperatures or expensive capital equipment.

The following represent examples of the production of microspheres according to this invention.

General Procedure

Ethyl cellulose (ethoxyl content 48%), was dissolved in dichloromethane to produce a 3.5% weight/volume polymer solution. Then, the indicated amount of diethyl phthalate was dissolved into that solution, followed by indicated amounts of the insecticide lambda-cyhalothrin. The amounts of lambda-cyhalothrin were chosen to provide between 100 to 300 weight percent of that substance relative to the amount of polymer dissolved in the solution.

The solution was then emulsified into an aqueous solution containing 5 weight percent polyvinyl alcohol and, at times, 0.01 weight percent sodium dodecyl sulfate. The mixture was then stirred for 15 minutes at room temperature at the indicated speeds; then a mercury vacuum (approximately 25 inch) was applied to remove the dichloromethane solvent. The microspheres were collected by filtration, resuspended in water containing 0.5 weight percent sodium dodecyl sulfate, and dried.

Comparison Examples

Using the same general procedure as above, but omitting the addition of diethyl phthalate, microspheres containing lambda-cyhalothrin were obtained.

The table summarizes the results of these experiments.

TABLE

| Experiment No. | Lambda-cyhalo-trin, wt. % | Ethyl cellulose, wt. % | Diethyl phthalate, wt. % | Stirring speed, rpm | Micro-sphere size, microns |
|---|---|---|---|---|---|
| Invention | | | | | |
| 1 | 40 | 40 | 5 | 800 | 65 |
| 2 | 41 | 41 | 5 | 2500 | 8 |
| Comparison (Tefft et al. process) | | | | | |
| A | 63 | 22 | — | 500 | 180 (est.) |
| B | 40 | 40 | — | 2500 | 11 |

The microcapsules prepared according to the invention were compared with those prepared according to the comparison example, by scanning electron microscope and regular microscope. It was observed that the microspheres prepared according to this invention were roughly spheroidal with an uneven outer surface and high porosity whereas those prepared according to the comparison example had smooth spherical surfaces with only a few pores visible.

Both types of microspheres were cut by a razor and again viewed. Those produced by the process of this invention were shown to have a highly porous surface and a highly porous internal structure as well, resembling a sponge. On the other hand, those produced in the comparison example appeared to have hollow cores with a number of small holes on the outer shell. This combination of porous, spongy structure makes the microspheres of the invention imminently suitable for applications in which a high loading of material to be dispensed, combined with a slow release rate, is desirable.

What is claimed is:

1. A process for producing porous spongy microspheres characterized by an uneven porous surface and a porous internal structure resembling a sponge having a diameter between about 3 and about 300 microns comprising: (a) preparing an organic phase comprising a solution of a polymer and a plasticizer selected from the group consisting of phthalate esters, phosphate esters, citrate, sebacate esters, glycerol, triacetin and acetylated monoglycerides, in an organic solvent; (b) preparing an aqueous phase comprising an aqueous solution of one or more emulsifying agents; (c) combining the organic and aqueous phases under emulsifying conditions to form an emulsion of the organic phase in the aqueous phase; and (d) evaporating the solvent to form said porous, spongy microspheres of uneven porous surface and a porous internal structure resembling a sponge.

2. A process according to claim 1 in which the microspheres further contain an ingredient to be dispensed, said ingredient to be dispensed being contained in the organic phase prepared in step (a).

3. A process according to claim 2 in which the ingredient to be dispensed is an agricultural chemical, a pharmaceutical, a medicine, a cosmetic or a fragrance.

4. A process according to claim 3 in which the ingredient to be dispensed is an agricultural chemical.

5. A process according to claim 1 in which the polymer is a cellulosic polymer.

6. A process according to claim 2 in which the polymer is a cellulosic polymer.

7. A process according to claim 1 in which the plasticizer is a phthalate ester.

8. A process according to claim 2 in which the plasticizer is a phthalate ester.

9. A process according to claim 1 in which the emulsifying agent comprises polyvinyl alcohol.

10. A process according to claim 2 in which the emulsifying agent comprises polyvinyl alcohol.

11. A process according to claim 1 in which the polymer is present in the organic phase in an amount of about 1 to about 50 weight percent and the plasticizer is present in the organic phase in an amount of about 0.1 and about 20 weight percent relative to the polymer.

12. A process according to claim 2 in which the microcapsules contain up to about 70 weight percent of the ingredient to be dispensed.

13. A process according to claim 12 in which the polymer is contained in the organic phase in am amount of between about 1 and about 50 weight percent and the plasticizer is contained in an amount of between about 0.1 and about 20 weight percent.

14. In a solvent evaporation process for producing microspheres containing an ingredient to be dispensed wherein an organic phase containing an ingredient to be dispensed and a polymer dissolved in an organic solvent is mixed with an aqueous phase containing an emulsifying agent to form an emulsion of the organic phase in the aqueous phase, the invention comprising including in the organic phase a plasticizer selected from the group consisting of phthalate esters, phosphate esters, citrate esters, sebacate esters, glycerol, triacetin and acetylated monoglyceride, said microspheres being characterized by an uneven porous surface and a porous internal structure resembling a sponge.

15. A process according to claim 14 in which the microspheres have a diameter of between about 3 and about 300 microns.

16. A process according to claim 14 in which the ingredient to be dispensed is present in the microspheres in an amount up to about 70 percent by weight.

17. A porous spongy microsphere product obtained by the process of claim 1, said product being characterized by an uneven porous surface and a porous internal structure resembling a sponge.

18. A porous spongy microsphere product obtained by the process of claim 2, said product being characterized by an uneven porous surface and a porous internal structure resembling a sponge.

19. A porous spongy microsphere product obtained by the process of claim 14, said product being characterized by an uneven porous surface and a porous internal structure resembling a sponge.

* * * * *